US012778428B2

(12) United States Patent
Yaroslavsky et al.

(10) Patent No.: US 12,778,428 B2
(45) Date of Patent: Nov. 3, 2026

(54) OPTICAL SENSOR FOR MONITORING TEMPERATURE-INDUCED CHANGES IN BIOLOGICAL TISSUES

(71) Applicant: UNIVERSITY OF MASSACHUSETTS, Boston, MA (US)

(72) Inventors: Anna N. Yaroslavsky, North Andover, MA (US); Tyler W. Iorizzo, Lithia, FL (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 18/683,122

(22) PCT Filed: Aug. 23, 2022

(86) PCT No.: PCT/US2022/075340
§ 371 (c)(1),
(2) Date: Feb. 12, 2024

(87) PCT Pub. No.: WO2023/028482
PCT Pub. Date: Mar. 2, 2023

(65) Prior Publication Data
US 2024/0324881 A1 Oct. 3, 2024

Related U.S. Application Data

(60) Provisional application No. 63/260,503, filed on Aug. 23, 2021.

(51) Int. Cl.
*A61B 5/01* (2006.01)
*A61B 5/00* (2006.01)
(Continued)

(52) U.S. Cl.
CPC .............. *A61B 5/0075* (2013.01); *A61B 5/01* (2013.01); *A61N 5/067* (2021.08); *A61N 2005/0628* (2013.01); *A61N 2005/063* (2013.01)

(58) Field of Classification Search
CPC ................................ A61B 5/0075; A61B 8/22
(Continued)

(56) References Cited

U.S. PATENT DOCUMENTS

2002/0084417 A1 7/2002 Khalil et al.
2005/0200843 A1 9/2005 Kumar et al.
(Continued)

FOREIGN PATENT DOCUMENTS

EP 3449815 A1 3/2019
WO 2021023780 A1 2/2021

OTHER PUBLICATIONS

International Search Report and Written Opinion for PCT Application No. PCT/US2022/075340, mailed on Jan. 19, 2023, 15 pages.

*Primary Examiner* — Boniface N Nganga
(74) *Attorney, Agent, or Firm* — BRAKE HUGHES BELLERMANN LLP

(57) ABSTRACT

The techniques described herein relate to a system including a light source configured to providing a beam of light to a sample of biological tissue, the light source including wavelengths over a range of at least 50 nm: a spectrometer configured for measuring a spectrum of an amount of light reflected from the biological tissue in response to the beam of light provided to the tissue; and a controller configured for directly correlating a temperature of the biological tissue with the spectrum of the light reflected from the biological tissue to determine a temperature of the biological tissue.

16 Claims, 16 Drawing Sheets

(51) Int. Cl.
*A61N 5/06* (2006.01)
*A61N 5/067* (2006.01)

(58) Field of Classification Search
USPC .......................................................... 600/549
See application file for complete search history.

(56) References Cited

U.S. PATENT DOCUMENTS

| | | | | |
|---|---|---|---|---|
| 2006/0111622 | A1 | 5/2006 | Merritt et al. | |
| 2008/0033300 | A1 | 2/2008 | Hoang et al. | |
| 2011/0066035 | A1 | 3/2011 | Norris et al. | |
| 2011/0077547 | A1* | 3/2011 | Baker, Jr. ................. | A61B 5/01 600/549 |
| 2020/0246072 | A1 | 8/2020 | Chia et al. | |

* cited by examiner

OPTICAL SENSOR FOR MONITORING TEMPERATURE-INDUCED CHANGES IN BIOLOGICAL TISSUES

CROSS REFERENCE TO RELATED APPLICATION

This application is a 35 U.S.C. § 371 National Phase Entry Application from PCT/US2022/075340, filed Aug. 23, 2022, designating the U.S., which claims priority to U.S. Provisional Application No. 63/260,503, titled “OPTICAL SENSOR FOR MONITORING TEMPERATURE-INDUCED CHANGES IN BIOLOGICAL TISSUES,” and filed on Aug. 23, 2021, the disclosures of which are incorporated herein by reference in their entireties.

TECHNICAL FIELD

This description relates to optical diagnosis and/or monitoring of biological tissues and, in particular, to techniques and optical sensors for monitoring temperature-induced changes in biological tissues.

BACKGROUND

Therapeutic and surgical applications of electromagnetic and sound waves (e.g., in the removal of cancer lesions, in lithotripsy, in port-wine stains removal, in photobiomodulation therapy, etc.) often cause an increase in temperature of the biological tissue with which the waves interact, and this increase in temperature may alter the properties of the target tissue and/or damage adjacent organs. Such changes have been reported in several tissues, including adipose, brain, skin, prostate, and liver. Thus, there is a great need to examine and monitor the effect of the thermal treatments on tissue temperature to ensure safe and effective delivery of light-based therapy, and consequently, temperature feedback is required for accurate dosimetry of thermal treatments. Currently, there is no technology that enables in vivo, non-invasive, and rapid temperature feedback.

However, measuring tissue temperature during therapeutic procedures is a challenging task. Some existing methods of temperature monitoring utilize thermocouples or fiber optic sensors, but both thermocouples and fiber optic sensors are invasive, as they require probes to be placed within the target tissue. Moreover, thermocouples tend to overestimate tissue temperature, and fiber optic sensors are susceptible to motion artifacts. Other existing methods of temperature monitoring utilize infrared sensors configured to measure a spectrum of infrared light emitted from a sample, which then is modelled as blackbody emitter, so that a temperature of the sample can be calculated based on the emitted infrared light. However, temperature measurement based on modelling a sample as a blackbody emitter can involve time-consuming calibration measurements of the ambient environment of the sample and/or the sensor and time-consuming calculations that fit measured quantities to a model of the sample, and such devices can be prone to inaccurate measurements due to inconsistent use or maintenance of the devices.

Therefore, the development of fast, non-invasive optical methods for assessing temperature remains an active area of clinical research.

SUMMARY

In some aspects, the techniques described herein relate to a system including: a light source configured to providing a beam of light to a sample of biological tissue, the light source including wavelengths over a range of at least 50 nm; a spectrometer configured for measuring a spectrum of an amount of light reflected from the biological tissue in response to the beam of light provided to the tissue; and a controller configured for directly correlating a temperature of the biological tissue with the spectrum of the light reflected from the biological tissue to determine a temperature of the biological tissue.

In some aspects, the techniques described herein relate to a system, wherein correlating the temperature of the biological tissue with the spectrum of the light reflected from the biological tissue includes correlating a wavelength of a water absorption peak in the measured spectrum with the temperature of the tissue.

In some aspects, the techniques described herein relate to a system, wherein correlating the temperature of the biological tissue with the spectrum of the light reflected from the biological tissue includes correlating a slope of the spectrum with the temperature of the biological tissue.

In some aspects, the techniques described herein relate to a system, further including an optical fiber configured for providing the beam of light to the biological tissue.

In some aspects, the techniques described herein relate to a system, further including an optical fiber configured for providing the light reflected from the biological sample to the spectrometer.

In some aspects, the techniques described herein relate to a system, further including: an illuminating optical fiber configured for providing the beam of light to the biological tissue, the illuminating optical fiber including a first end located proximate to the biological tissue from which the beam of light is provided to the biological sample; and a plurality of detection optical fibers, each detection optical fiber having a second end configured for collecting the light reflected from the biological sample and for providing the collected light to the spectrometer.

In some aspects, the techniques described herein relate to a system, wherein each of the second ends is located at a different distance from the first end from which the beam of light is provided to the biological sample.

In some aspects, the techniques described herein relate to a system or claim 6, further including: a heating optical fiber configured for providing radiation to the biological sample to heat the biological sample, wherein each of the illuminating optical fiber, the plurality of detection optical fibers, and the heating optical fiber are contained withing a common fiber bundle.

In some aspects, the techniques described herein relate to a system, further including: an plurality of illuminating optical fibers configured for providing the beam of light to the biological tissue, each of the illuminating optical fiber including a first end located proximate to the biological tissue from which the beam of light is provided to the biological sample; and a detection optical fiber having a second end configured for collecting the light reflected from the biological sample and for providing the collected light to the spectrometer.

In some aspects, the techniques described herein relate to a system, wherein each of the first ends is located at a different distance from the second end from which the beam of light is provided to the biological sample.

In some aspects, the techniques described herein relate to a system further including: a heating optical fiber configured for providing radiation to the biological sample to heat the biological sample, wherein each of the plurality of illuminating optical fibers, the detection optical fiber, and the heating optical fiber are contained withing a common fiber bundle.

In some aspects, the techniques described herein relate to a system, wherein the spectrometer is configured for measuring the spectrum of the amount of light reflected from the biological tissue in response to the beam of light provided to the tissue as the biological tissue is heated; and wherein the controller is configured for directly correlating a temperature of the biological tissue with a change of spectrum of the light reflected from the biological tissue as the biological tissue is heated to determine a temperature of the biological tissue.

In some aspects, the techniques described herein relate to a system, wherein the change in the spectrum includes a change in a wavelength of a water absorption peak in the measured spectrum as the biological tissue is heated.

In some aspects, the techniques described herein relate to a system, wherein the change in the spectrum includes a change in the slope of the spectrum with the temperature of the biological tissue as the biological tissue is heated.

DETAILED DESCRIPTION

In implementations of the techniques described herein, a temperature of biological tissue exposed to light can be correlated with measurements of the light that interacts with the tissue, such that the optical measurements can be used to measure a temperature of the tissue. In particular, a spectrum of broadband light reflected from the biological tissue can be directly correlated with a temperature of the tissue, without calculating any optical properties (e.g., an absorption coefficient, a scattering coefficient, an anisotropy factor, etc.) of the tissue from the spectrum.

The devices and techniques described herein can be used to facilitate accurate, non-invasive measurements of a temperature of biological tissue, for example, when the biological tissue is undergoing thermal treatment that transfers heat to the tissue and causes the temperature of the tissue to rise. Such accurate, non-invasive measurements of a temperature of biological tissue can facilitate accurate and safe removal of cancer lesions via a thermal treatment of the cancerous tissue and can enable accurate dosimetry of other thermal and photothermal treatments, such as, for example, lithotripsy, port-wine stains removal, and photobiomodulation therapy.

The inventor performed experiments in which light was provided to biological tissue (tissue from the ear or a living mouse and ex vivo human skin tissue) and the diffuse reflectance spectrum from the tissue was measured for different temperatures of the biological tissue. In some experiments, the total transmittance spectrum and the diffuse transmittance spectrum though the biological tissue also was measured. From the measurements, correlations between the raw measured spectra and the temperature of the biological tissue and between optical properties of the biological tissue calculated from the raw measured spectra and the temperature of the biological tissue were determined. Based on the observed correlations between the raw measured spectra and the temperature of the biological tissue, a system is proposed that determines a temperature of biological tissue based directly on a measured optical reflectance spectrum obtained from the tissue.

Figure 1A:
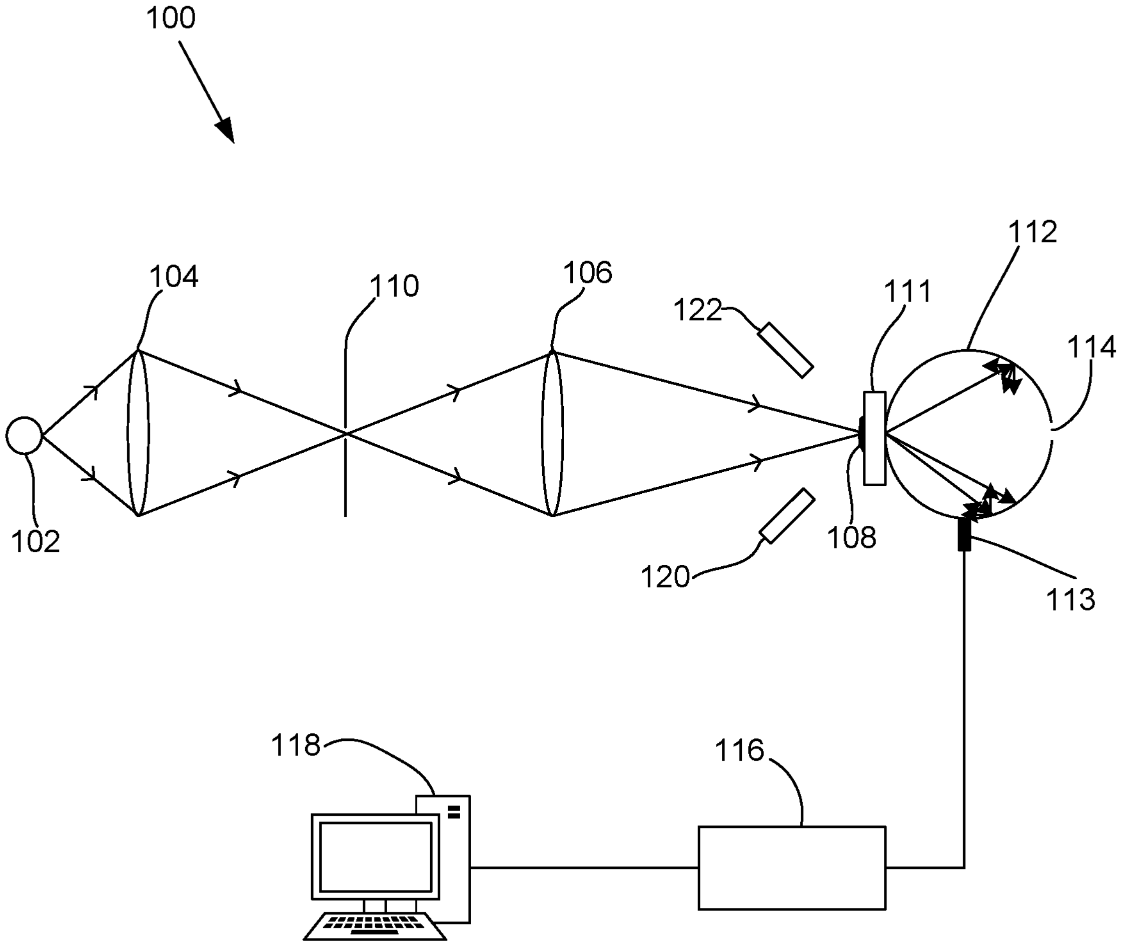
FIG. 1A is a schematic diagram of a system for measuring total and diffuse transmittance of a sample.

FIG. 1A is a schematic diagram of a system 100 for measuring total and diffuse transmittance of a sample. The system includes a light source 102 that provides broad bandwidth light that is focused, for example, by lenses 104, 106 onto a sample 108. The provided light can pass through a pinhole 110 to improve the quality of the focus of the light. The sample 108 is mounted on a stage 111 that includes a transparent portion though which the provided light can pass after interacting with the sample 108. The stage 111 can be coupled to a heat source to maintain the stage 111 and the sample 108 at a fixed temperature. The light that passes through the sample can be detected by an integrating sphere 112 coupled to a detector 113 and spectra of the detected light can be measured by a spectrometer 116. The integrating sphere 112 includes a closable exit port 114 that can be closed to measure a total transmittance spectrum and that can be opened to allow un-scattered light to exit the integrating sphere, so that a diffuse transmittance spectrum can be measured. The spectra can be further analyzed (e.g., to calculate optical properties of the sample 108) by a computer 118.

Figure 1B:
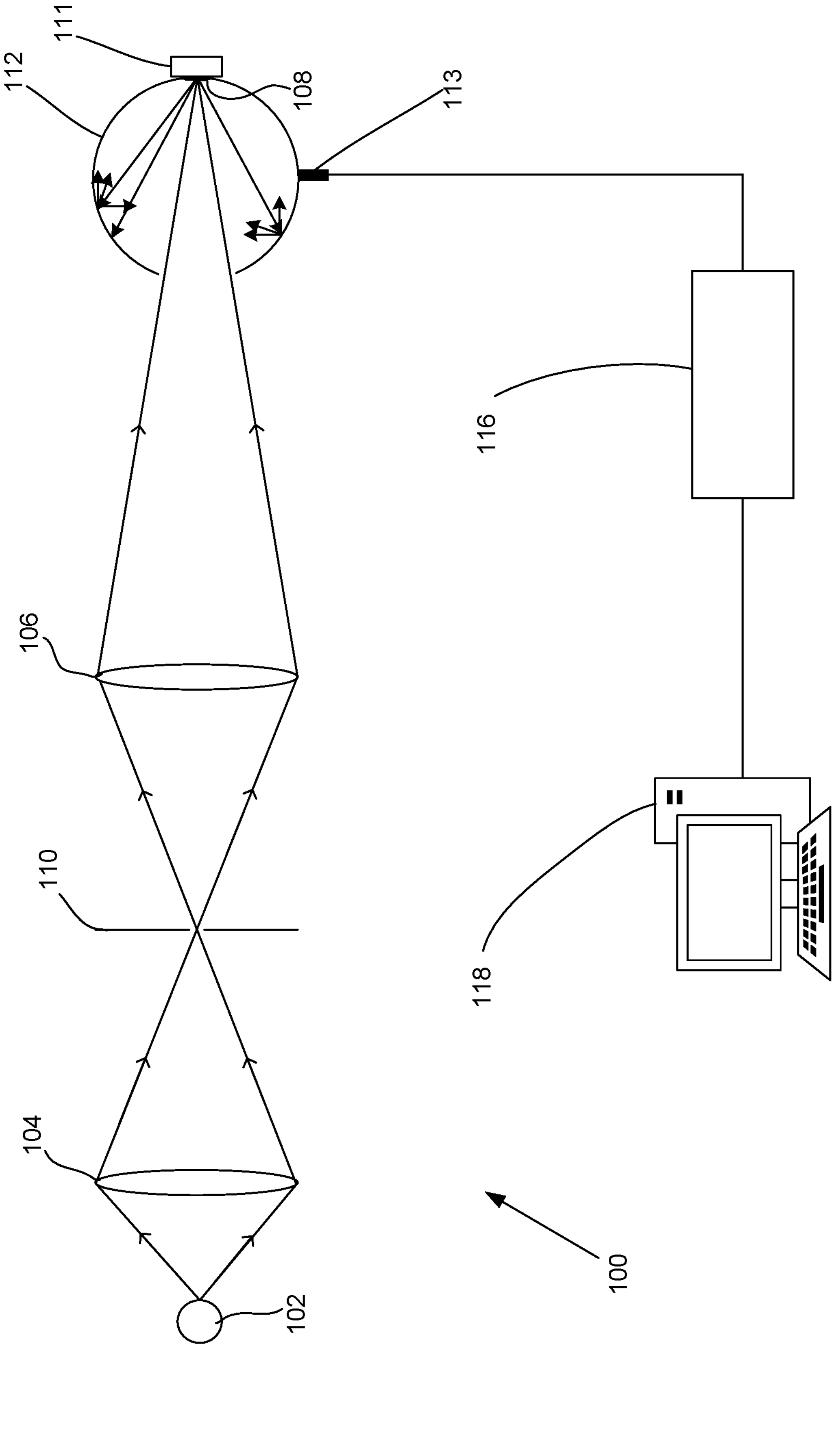
FIG. 1B is a schematic diagram of the system of FIG. 1A when configured for measuring diffuse reflectance of the sample.

FIG. 1B is a schematic diagram of the system 100 when configured for measuring diffuse reflectance of the sample 108. The light provided from the light source 102 is focused onto the sample 108 that is mounted on the heated stage 111, and light reflected from the sample 108 is collected by an integrating sphere 112 coupled to a detector 113, and spectra of the collected light are measured by a spectrometer 116. A 99% spectralon diffuse reflectance standard can be used as a calibration a reference. Light that is transmitted through the sample 108 without being reflected can exit the integrating sphere 112 and through a transparent portion of the stage 111. The measured spectra can be further analyzed (e.g., to calculate optical properties of the sample 108) by a computer 118.

In some experiments, the diffuse reflectance, the total transmittance, and the diffuse transmittance from living mouse ears were measured over a spectral range 400 nm to 1650 nm using the systems of FIGS. 1A and 1B with the mouse ear tissue held at temperatures of 25° C., 36° C. and 60° C. During the experiments, the temperature of the biological tissue sample 108 was monitored using an infrared thermal camera 120.

Temperature-induced morphological changes of the sample 108 were monitored using a reflectance confocal microscope 122. The microscope 122 provided lateral and axial resolution of 1.5 μm and 5 μm, respectively, and the imaging depth was approximately 100 μm with a field of view of 800×600 $\mu m^2$. Confocal images and videos were acquired as the mouse ear tissue was heated from 25° C., to 60° C.

Figure 2B:
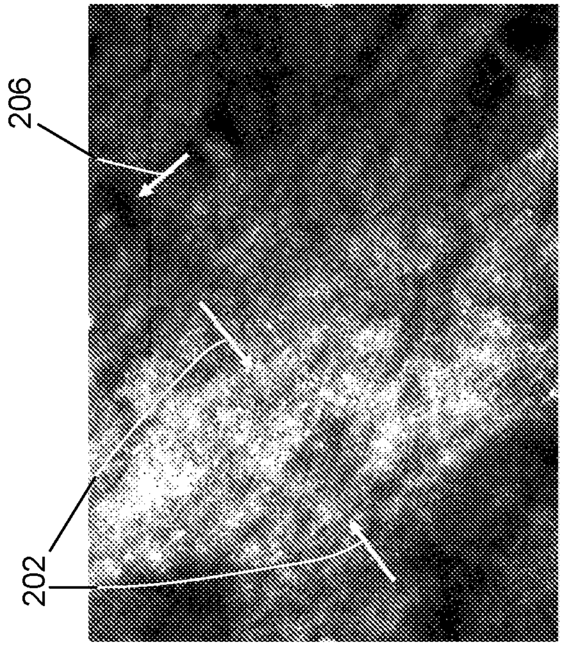
FIGS. 2A and 2B are image frames of mouse ear skin sample acquired at 25° C. and 60° C., respectively.
Figure 2A:
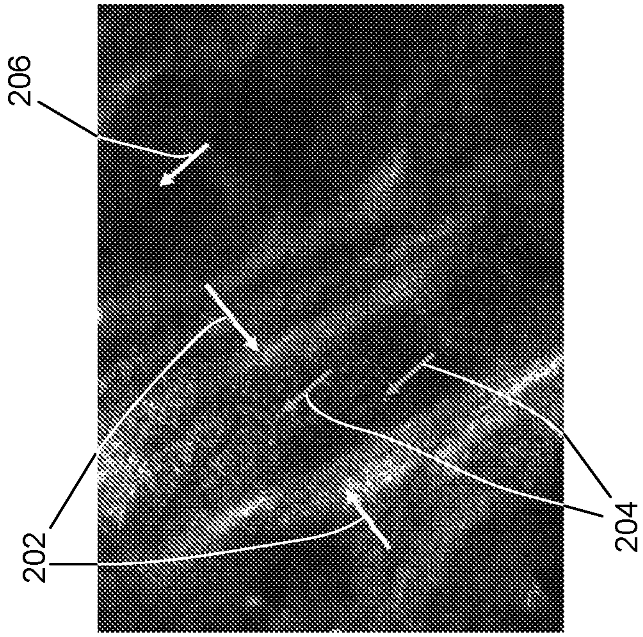

Two image frames of mouse ear skin sample acquired with a field of view of 750 μm×560 μm at 25° C. and 60° C. are shown in FIG. 2A and FIG. 2B, respectively. Arrows 202 and arrows 204 point to a vascular wall of a blood vessel of the sample and to highly scattering erythrocytes inside the blood vessel, respectively. Arrows 206 point to a hair follicle that appears dark due to lack of melanin in albino mice. The features shown by arrows 202, 204, and 206 in FIG. 2A, obtained at 25° C. are different in FIG. 2B, obtained at 60° C. because the higher temperature causes tissues coagulate and shrink. The coagulation process is accompanied by collagen swelling, homogenization, and collapse of the blood vessel walls, and destruction of the erythrocytes, and all these changes are evident in the comparison of the images in FIGS. 2A and 2B, which show that the reflectance signal from swollen collagen increases, hair follicles shrink, and the blood vessel, present in FIG. 2A, disappears at the higher temperature.

From the measured transmittance and reflectance spectra, optical properties of the sample (e.g., absorption, scattering, and anisotropy factors) were calculated using an inverse Monte Carlo technique. The Monte Carlo technique accounted for the exact geometrical and optical parameters of the experimental arrangement, the multi-layer structure of the object under investigation (i.e., the biological tissue sample and transparent slides and other media used to support the sample) and losses of light at the edges of the mouse ear tissue sample. The MC technique was incorporated as a forward procedure into a quasi-Newton inverse algorithm. The inverse algorithm employed a Broyden update formula to reduce the number of the forward model calls and the "trust region" approach to achieve proximity of the solution even when the initial approximation was poor. The inverse technique allowed determination of absorption coefficients, scattering coefficients, and anisotropy factors from the measurements of total transmittance, collimated transmittance, and diffuse reflectance, while parameters of the phase function were pre-set. The anisotropy factors were determined under the assumption of the Henyey-Greenstein scattering phase function. The MC technique is computationally intense and time consuming.

Figure 3A:
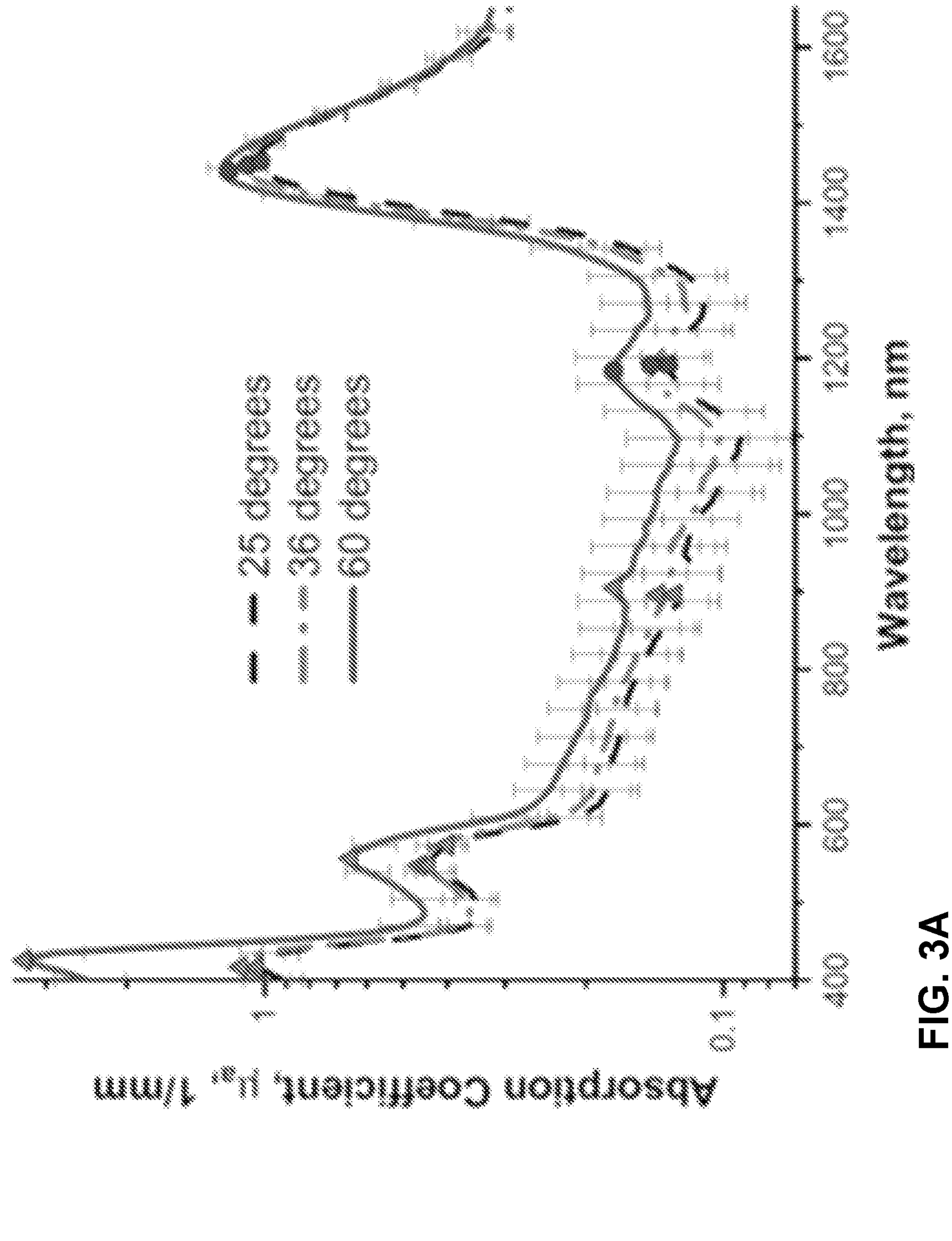
FIGS. 3A, 3B, and 3C are graphs of absorption bands of mouse ear skin over different ranges of wavelengths.
Figure 3B:
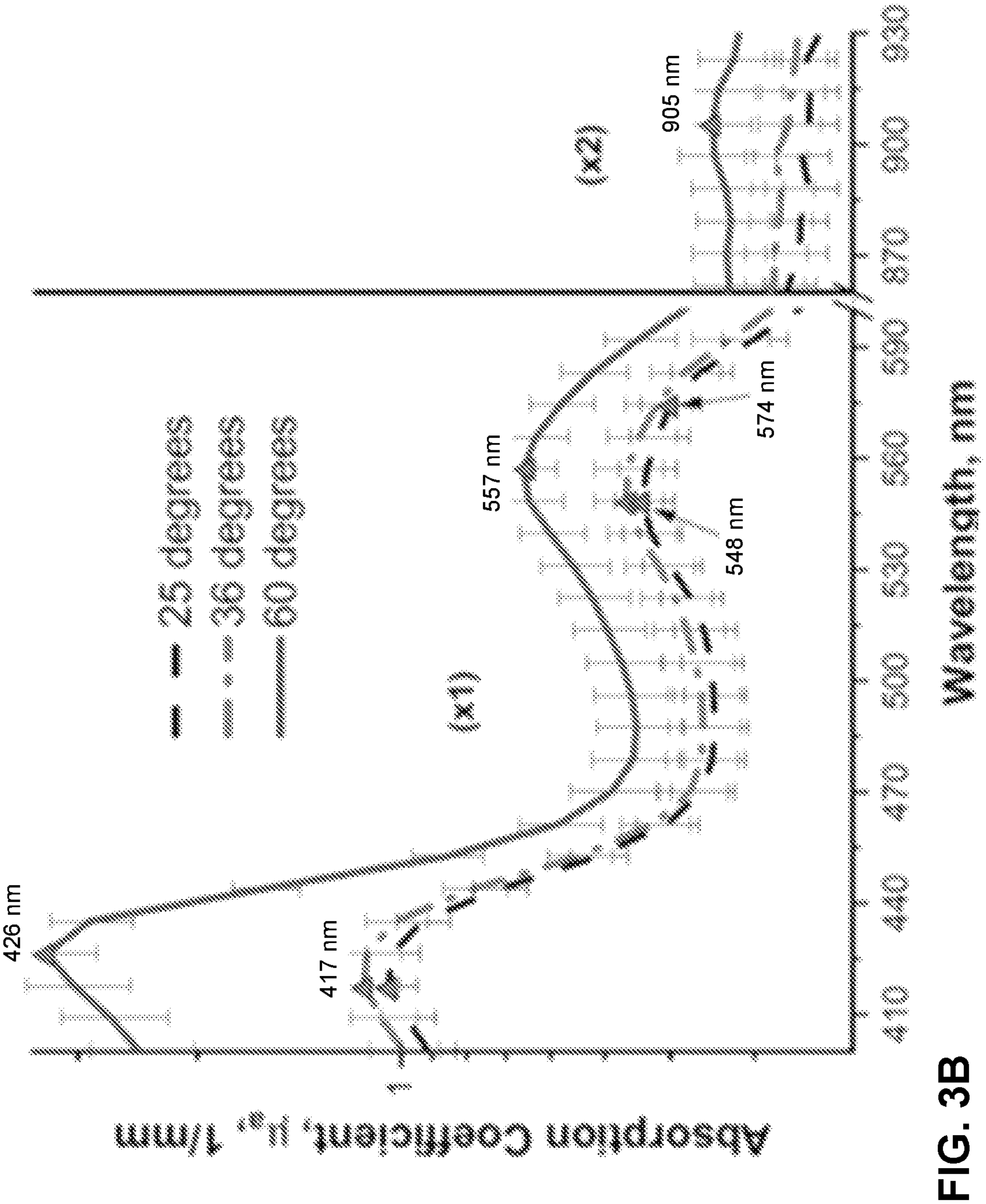
Figure 3C:
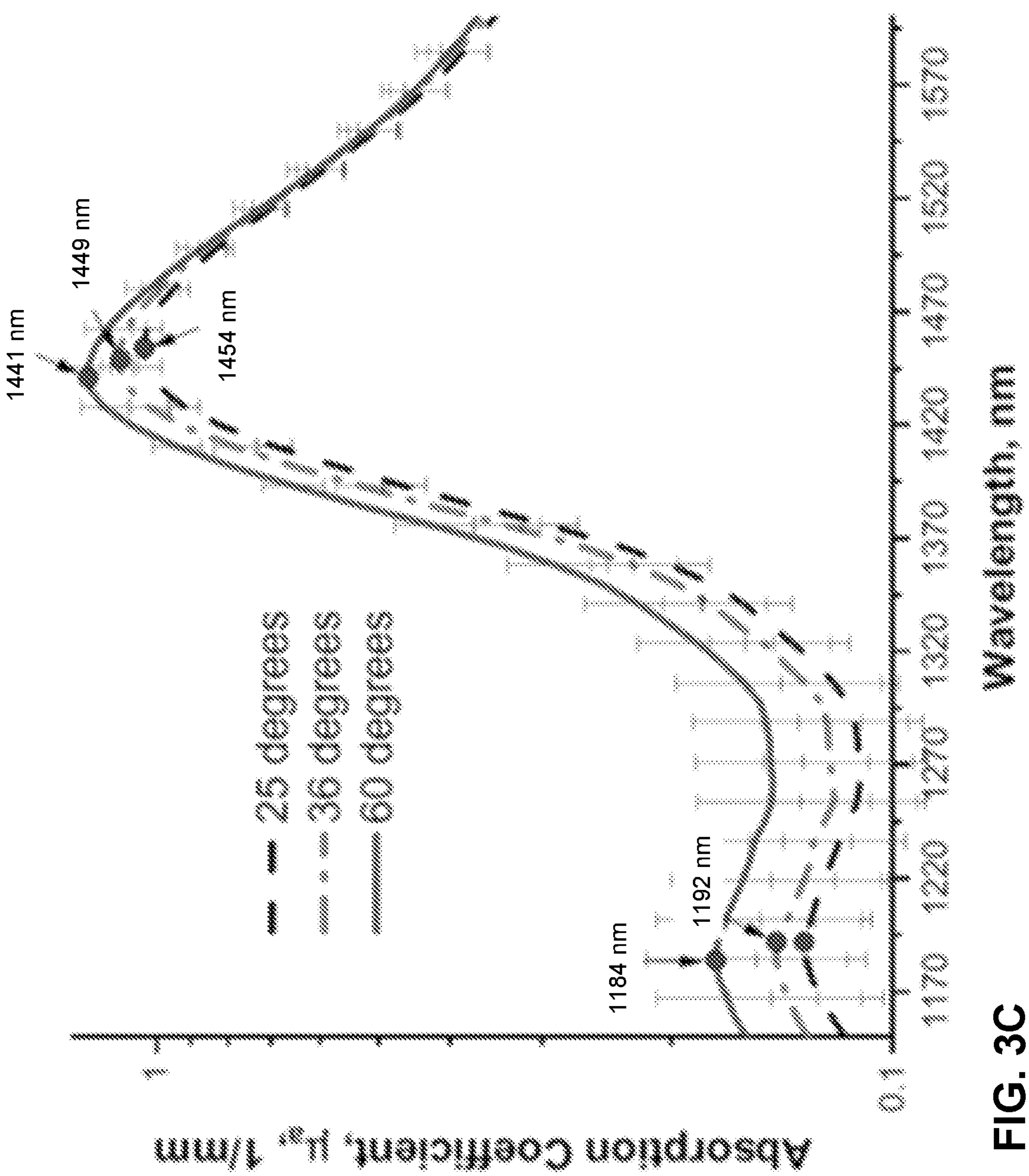

The calculated optical properties of the mouse ear specimen obtained at different temperatures and at different wavelengths are presented in FIGS. 3A, 3B, and 3C. FIG. 3B shows a magnified view of the absorption bands between 400 and 930 nm. It can be readily appreciated that the Soret absorption band of hemoglobin exhibits a red shift from 417 nm at the lower temperatures to 426 nm at 60° C. Even though ketamine-xylazine anesthetic reduces hemoglobin oxygenation, a double absorption peak of oxyhemoglobin between 545 and 575 nm is discernible at the lower temperatures, which is replaced by a single peak of deoxyhemoglobin at approximately 557 nm at 60° C. In addition, a deoxyhemoglobin absorption band appears around 905 nm. FIG. 3C is a magnified view of the absorption bands between 1150 and 1600 nm showing two water absorption peaks in the proximity of 1200 nm and 1450 nm. Both peaks exhibit considerable blue shifts (i.e., shifts to shorter wavelength) as the tissue temperature increased to 60° C. from 25° C. and 36° C. Specifically, the water absorption peak shifts from 1192 nm at 25° C. and 36° C., to 1184 nm at 60° C., whereas the absorption peak located at 1454 nm at 25° C. shifts to 1449 nm at 36° C. and to 1441 nm at 60° C. Statistical analysis confirmed that the blue shifts in water absorption as temperature increased from 25 to 60° C. were highly significant ($P<0.0001$).

Figure 4A:
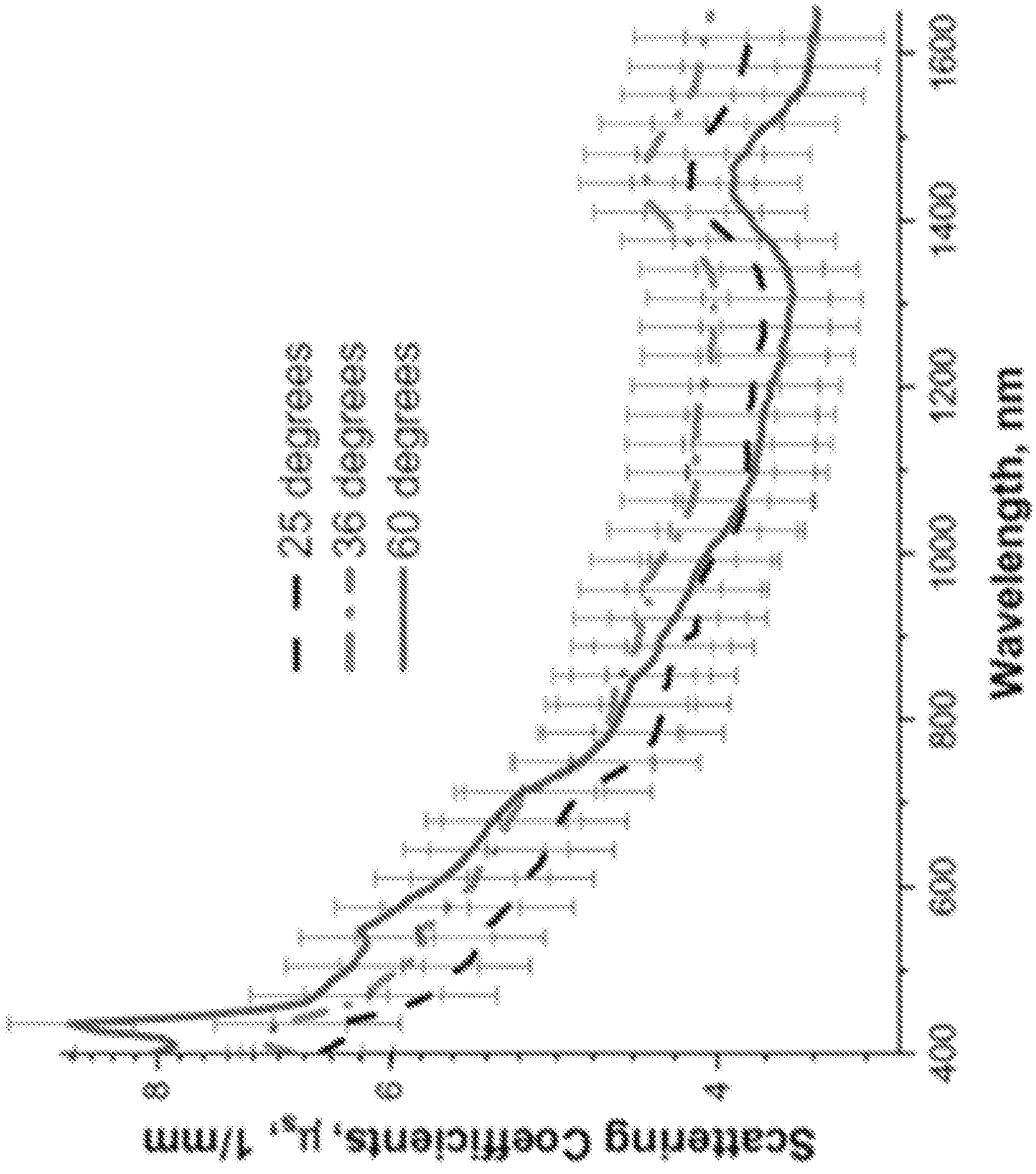
FIGS. 4A, 4B, and 4C are graphs calculated scattering coefficients, anisotropy factors, and reduced scattering coefficients for mouse ear skin at different temperatures and at different wavelengths.
Figure 4B:
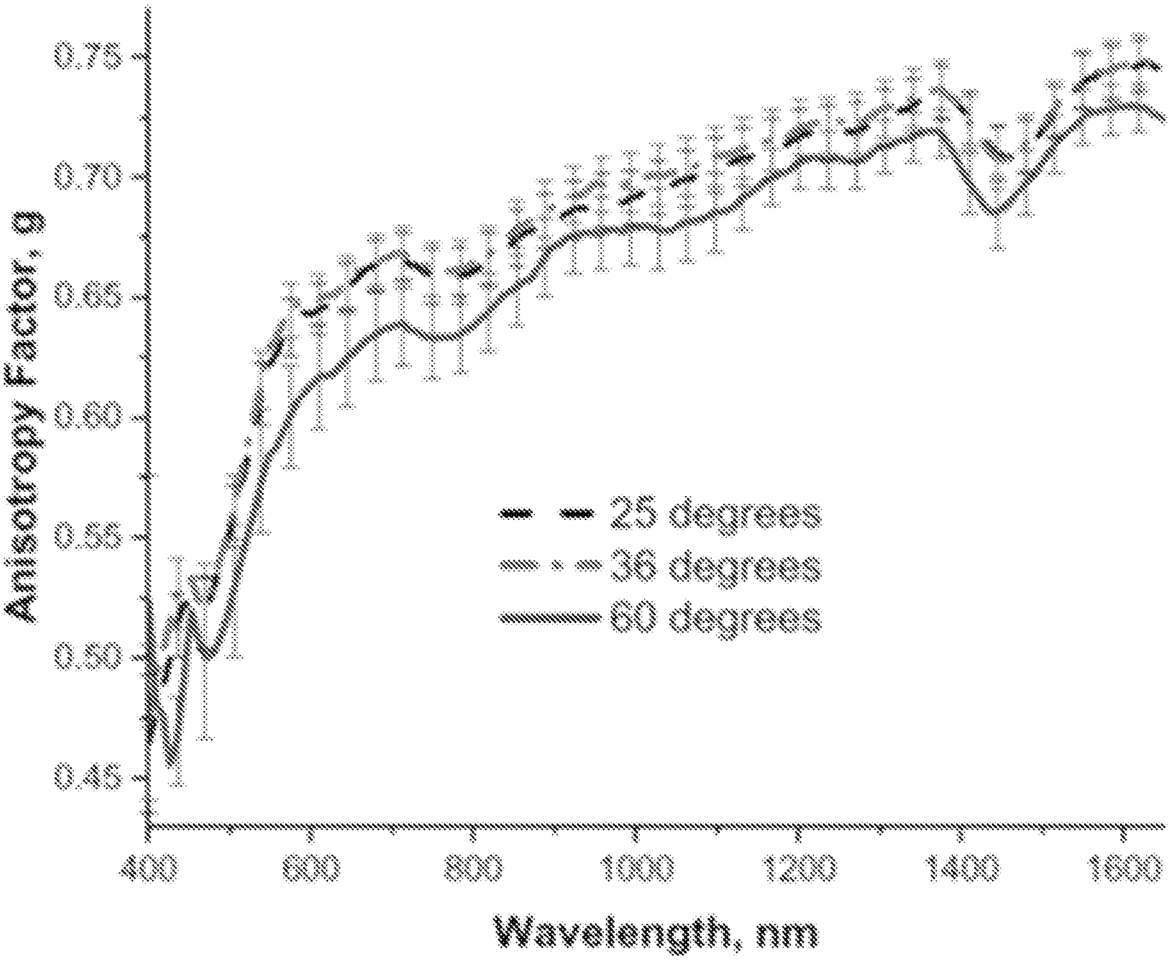
Figure 4C:
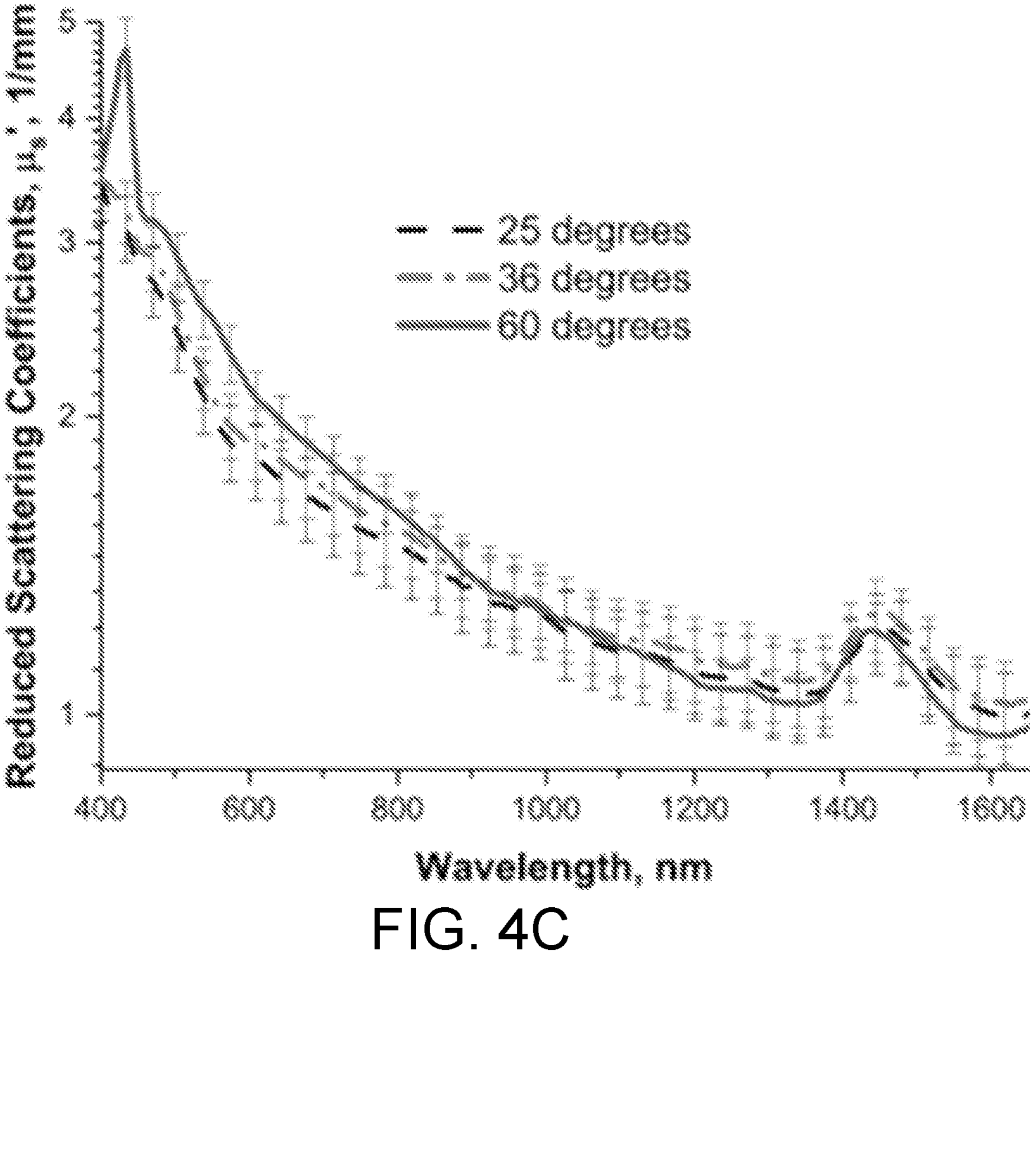

Calculated scattering coefficients (μs), anisotropy factors (g), and reduced scattering coefficients (μs'), at all the temperatures investigated are shown in FIGS. 4 (*a*), 4 (*b*), and 4 (*c*). The scattering coefficients (FIG. 4 (*a*)) were found to decrease with increasing wavelength at each temperature, with stronger spectral dependence at 60° C., as compared to 25° C. and 36° C. The much steeper slope of the scattering coefficient versus wavelength graph at 60° C. may be explained by tissue coagulation that causes destruction of the larger scatterers, such as erythrocytes, as well as homogenization of the blood vessel walls and collagen bundles in the dermis. Accordingly, the anisotropy factors, displayed in FIG. 4 (*b*), are slightly lower at 60° C. Similar to the scattering coefficients, the reduced scattering coefficients presented in FIG. 4 (*c*) demonstrate a steeper gradient at 60° C., as compared to those observed at 25° C. or 36° C.

The optical data were evaluated statistically to obtain least squares estimates of mean gradient (slopes of scattering and reduced scattering coefficients) or shifts of absorption maxima, along with corresponding standard errors, for each temperature group. A mixed effects model was used to assess differences between gradients and extremum shifts observed at 25° C./60° C. and 36° C./60° C. with $P\leq0.05$ considered significant.

The experimental results indicated significant differences between the optical properties of skin at different temperatures. Absorption and scattering coefficients increased, whereas anisotropy factors decreased, with increasing temperature. Changes in absorption coefficients indicate deoxygenation of hemoglobin, and a blue shift of water absorption bands. Confocal imaging confirmed that the experimental observations can be explained by temperature-induced protein denaturation and blood coagulation in the skin tissue.

Comparison of the differences between the calculated optical properties of skin at different temperatures obtained by reflectance confocal microscopy with the physical changes to the tissue sample due to the increased temperature of the sample demonstrates that the major differences in absorption are caused by deoxygenation of blood and heating of water, while the major differences in scattering are caused by blood and collagen coagulation.

The inventor also performed experiments in which light was provided to ex vivo freshly excised human skin tissue reflected light was collected through an end of an optical fiber and provide by the fiber to a spectrometer that reflectance spectrum from the tissue for different temperatures of the tissue. From the measurements, correlations between the raw measured spectra and the temperature of the biological tissue was determined. Based on the observed correlations between the raw measured spectra and the temperature of the biological tissue, the inventors determined that raw reflectance spectrum measured can be used as a reliable metric for determining a temperature of biological tissue, where the determined is based directly on a measured optical reflectance spectrum obtained from the tissue is not based on correlations with any calculated optical properties of the sample.

Figure 5:
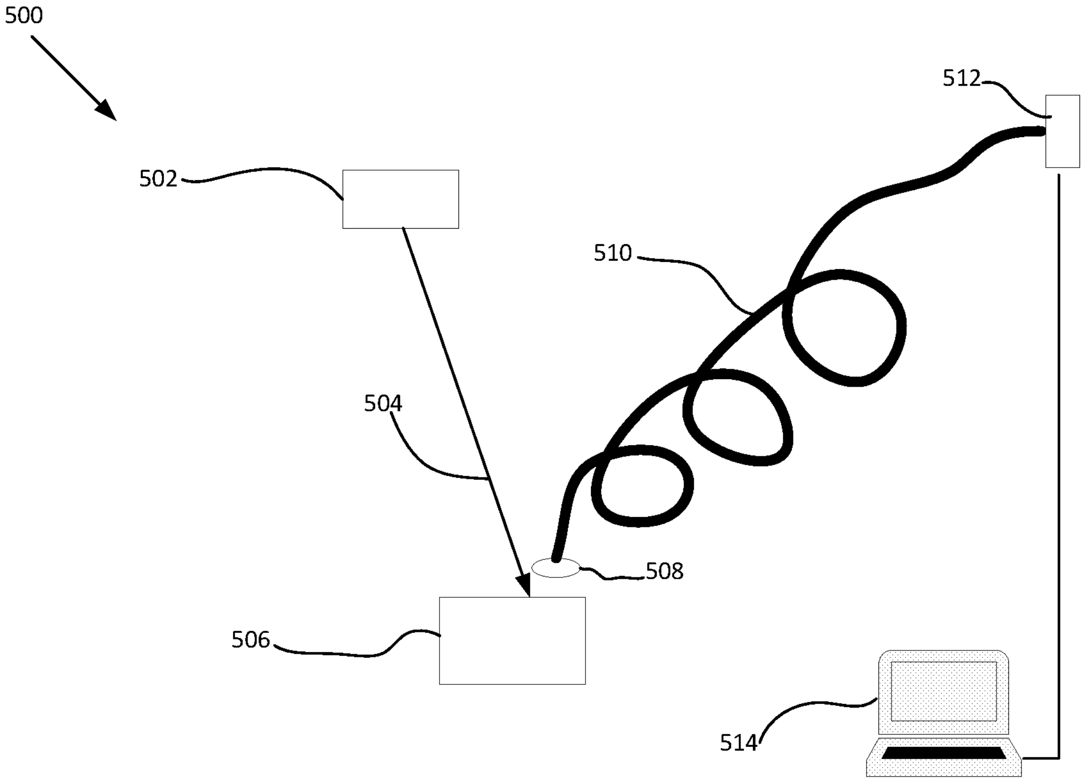
FIG. 5 is an example schematic diagram of a system for measuring a temperature of biological tissue based directly on reflectance spectra measurements of the biological tissue.

FIG. 5 is an example schematic diagram of a system 500 for measuring a temperature of biological tissue based directly on reflectance spectra measurements of the biological tissue. The system 500 can include a light source 502 that emits light over a range of wavelengths. For example, the light source 502 can include a halogen light source that emits a continuous spectrum of light over a range of visible and near infrared wavelengths. The light 504 from the light source 502 can be provided to a biological tissue sample 506, for example, in the form of a focused spot. In some implementations, the focused spot can have a FWHM diameter of less than 5 mm. In some implementations, the light 504 can be provided through an optical fiber. Light reflected by the sample 506 in response to the light 504 that is provided to the sample can be collected (optionally by a lens 508), and the collected light can be provided to a spectrometer 512 (e.g., an InGaAs spectrophotometer that operates over a wavelength range of about 900 nm to about 1700 nm) that measures the spectrum of the collected reflected light. In some implementations, the collected light can be provided to the spectrometer 512 by way of an optical fiber 510. The measured spectrum is based on measurements of an amount of reflected light received (e.g., an amplitude, an intensity, or a power of light received) by the spectrometer at different wavelengths with the range of wavelengths over which the spectrometer operates. A 99% spectralon diffuse reflectance standard can be used as a calibration a reference. For example, the light 504 from the light source 502 can be provided to a 99% spectralon diffuse reflectance standard, and the spectrum of reflected light can be measured for different total powers or intensities of the provided light, in order to established a baseline reflectance amount for the light at different wavelengths for different total powers. Then, when the power or intensity of light reflected from the sample 506 is measured it can be compared to the baseline to determine a reflectance percentage for different wavelengths of the reflected spectrum.

The spectrum of the collected light can be analyzed to determine a temperature of the biological tissue based on the wavelength of the water absorption peaks in the spectrum (e.g., manifested as dips in the measured reflected values near 980 nm, 1180 nm, and 1450 nm) and/or based on a slope of the reflectance versus wavelength curve (e.g., in a range of wavelengths between 900 nm and 1100 nm).

The system 500 can include a controller 514 that can include a processor and a memory storing instructions that are executable by the processor to perform the techniques described herein. For example, the memory of the controller 514 can include one or more look-up tables for the temperature-dependent reflectance spectra that correlate measured optical properties of the spectra with temperatures of the biological tissue.

In some implementations, the light 504 from the light source 502 can be provided to the sample 506 through the optical fiber 510 and lens 508 or through another optical fiber adjacent to the fiber 510 used to receive and pass the collected light to the spectrometer 512. In some implementations, the lens 508 and the optical fiber 510 can be integrated with a tool that is used to provide a light-, sound-, and/or heat-based therapy to the biological tissue, so that the temperature of the biological tissue can be continuously while the therapy is provided to the sample.

Figure 6A:
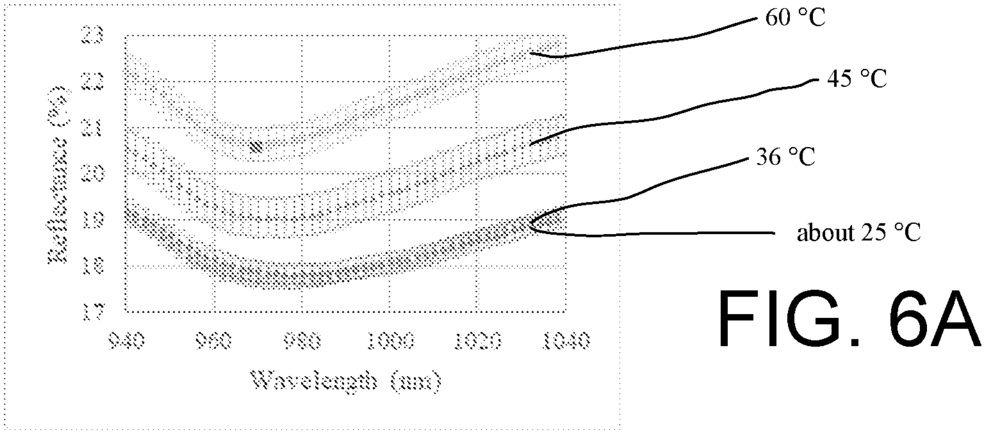
FIGS. 6A, 6B, and 6C are graphs of reflectance spectra collected from human skin tissue measured over different wavelength ranges for tissue temperatures of 25, 36° C., 45° C., and 36° C.
Figure 6B:
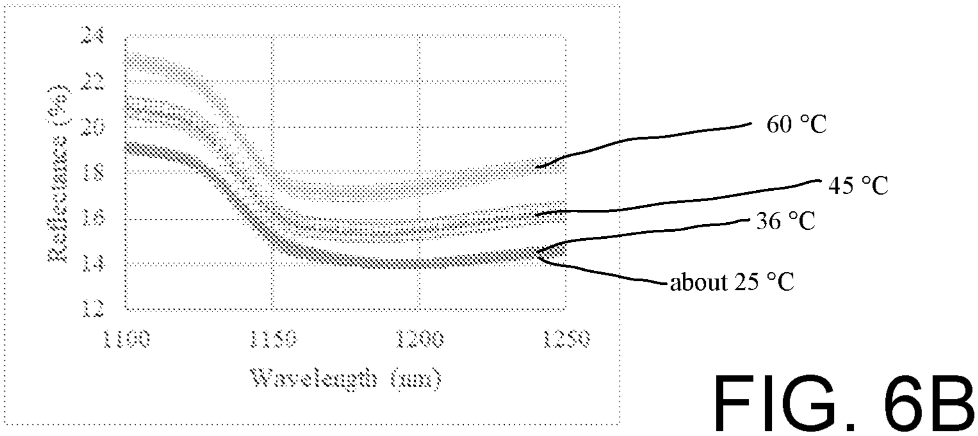
Figure 6C:
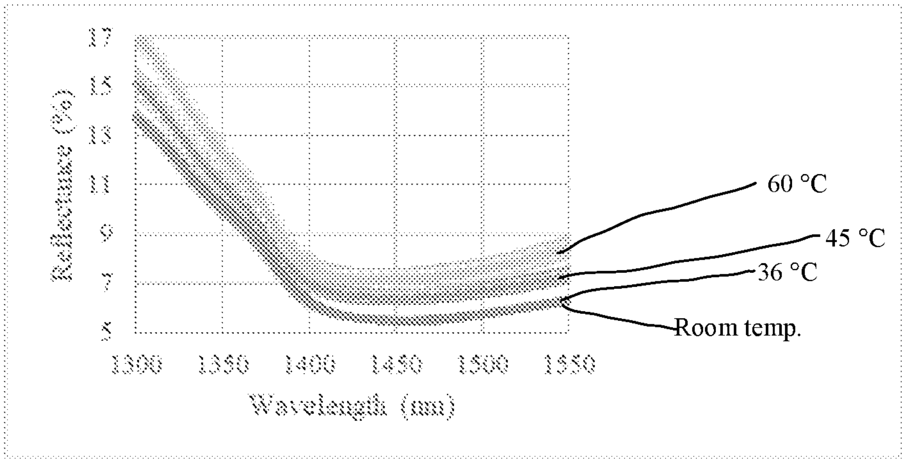

FIG. 6A is a graph of reflectance spectra (i.e., graphs of values of an amount of reflected light at different wavelengths or of reflectance percentages for the different wavelengths) collected from human skin tissue measured over a wavelength range from 940 nm to 1040 nm for tissue temperatures of room temperature (about 25° C.) (round icons for data points), 36° C. (diamond icons for data points), 45° C. (triangle icons for data points), and 60° C. (square icons for data points). FIG. 6B is a graph of reflectance spectra (i.e., graphs of values of an amount of reflected light at different wavelengths) collected from human skin tissue measured over a wavelength range from 1100 nm to 1250 nm for tissue temperatures of room temperature (about 25° C.) (round icons for data points), 36° C. (diamond icons for data points), 45° C. (triangle icons for data points), and 60° C. (square icons for data points). FIG. 6C is a graph of reflectance spectra (i.e., graphs of values of an amount of reflected light at different wavelengths) collected from human skin tissue measured over a wavelength range from 1300 nm to 1550 nm for tissue temperatures of room temperature (about 25° C.) (round icons for data points), 36° C. (diamond icons for data points), 45° C. (triangle icons for data points), and 60° C. (square icons for data points). The reflectance values on the y-axes of the graphs are expressed as percentages, meaning the percent of light that is reflected from the sample at a particular wavelength, compared to the amount of light that is provided to the sample at the particular wavelength.

It can be seen from the spectra plotted in each of FIGS. 6A, 6B, and 6C that the reflectance values near the water absorption peaks close to 980 nm, 1200 nm, and 1450 nm increase with increasing temperature of the biological tissue. This change in the reflectance value can be used to determine a temperature of the biological tissue.

The spectral data obtained at the different wavelengths and different temperatures were fitted to determine the values of the absorption peaks near 980 nm, 1180 nm, and 1450 nm at the different temperatures, and these values are presented below in Table 1 for healthy human skin and in Table 2 for cancerous human skin.

TABLE 1

Normal Human Tissue Absorption Peak Wavelengths

| Temperature | 900-1000 nm Peak | | | | 1100-1200 nm Peak | | | | 1450 nm Peak | | | |
|---|---|---|---|---|---|---|---|---|---|---|---|---|
| (degrees C.) | Average | St Dev | Blue Shift | St Dev | Average | St Dev | Blue Shift | St Dev | Average | St Dev | Blue Shift | St Dev |
| 25 | 979 | 3 | 0 | — | 1200 | 2 | 0 | — | 1452 | 3 | 0 | — |
| 36 | 977 | 2 | 2 | 1 | 1198 | 4 | 2 | 2 | 1448 | 3 | 4 | 2 |

TABLE 1-continued

| Normal Human Tissue Absorption Peak Wavelengths | | | | | | | | | | | | |
|---|---|---|---|---|---|---|---|---|---|---|---|---|
| Temperature | 900-1000 nm Peak | | | | 1100-1200 nm Peak | | | | 1450 nm Peak | | | |
| (degrees C.) | Average | St Dev | Blue Shift | St Dev | Average | St Dev | Blue Shift | St Dev | Average | St Dev | Blue Shift | St Dev |
| 45 | 976 | 2 | 4 | 2 | 1196 | 5 | 4 | 3 | 1447 | 3 | 5 | 1 |
| 60 | 974 | 1 | 5 | 2 | 1194 | 5 | 6 | 3 | 1441 | 2 | 11 | 2 |

TABLE 2

| Cancer Lesion Human Tissue Absorption Peak Wavelengths | | | | | | | | | | | | |
|---|---|---|---|---|---|---|---|---|---|---|---|---|
| Temperature | 900-1000 nm Peak | | | | 1100-1200 nm Peak | | | | 1450 nm Peak | | | |
| (degrees C.) | Average | St Dev | Blue Shift | St Dev | Average | St Dev | Blue Shift | St Dev | Average | St Dev | Blue Shift | St Dev |
| 25 | 976 | 2 | 0 | — | 1199 | 3 | 0 | — | 1453 | 5 | 0 | — |
| 36 | 973 | 2 | 3 | 1 | 1195 | 5 | 3 | 2 | 1449 | 5 | 3 | 3 |
| 45 | 970 | 3 | 6 | 1 | 1193 | 6 | 6 | 3 | 1446 | 4 | 6 | 4 |
| 60 | 969 | 3 | 8 | 2 | 1188 | 7 | 11 | 5 | 1440 | 4 | 13 | 5 |

Based on experiments performed by the inventors, it has been determined that reflectance measurements on normal human skin tissue in the vicinity of the 1450 nm water absorption peak exhibited a blue shift of 5±1 nm as the temperature increased from 25° C. to 36° C., and 11±1 nm as the tissue temperature increased from 25° C., to 60° C. and that reflectance measurements on cancerous skin tissue in the vicinity of the 1450 nm water absorption peak exhibited a blue shift of 4±1 nm as the temperature increased from 25° C. to 36° C., and 7±1 nm as the tissue temperature increased from 25° C., to 60° C. In addition, it is expected that, similar to the reflectance spectra collected from mouse ears, the absolute value of the slope of the reflectance spectra between 800 nm and 1100 nm and between 900 nm and 1100 nm collected from human tissue at 60° C. will be greater than the absolute value of the slope of the reflectance spectra between 800 nm and 1100 nm and between 900 nm and 1100 nm collected from human tissue at 25° C. or 36° C.

As both the blue shift of the water absorption band in the vicinity of 1450 nm and the increase in the absolute value of the slope of the reflectance spectrum in the 900 nm-1100 nm range can be detected by examination of the measured diffuse reflectance spectra in the 900 nm-1700 nm wavelength range, a sensor (e.g., an optical fiber-optic sensor) can be used to monitor the diffuse reflectance spectra from biological tissue for real-time assessment of temperature during thermal treatments.

Thus, by acquiring and analyzing diffuse reflectance spectra in the range between 900 nm and 1700 nm, and by detecting the change of the slope of the reflectance curve in the range between 900 nm and 1100 nm and measuring the blue shift of the water absorption band around 1450 nm and other absorption peaks, we can reliably monitor the temperature of biological tissue between 25 and 60° C.

In particular, a blue shift of spectral peak due to water absorption of the light, and an increase in the absolute value of the slope of a curve of the scattering of the light as a function of wavelength in the 900 nm-1100 nm range, can be detected directly from the measured reflectance values and can be correlated with a change of temperature of the tissue from which the reflected light is received.

In some implementations, a change of spectrum of the light reflected from the biological tissue as the biological tissue is heated to determine a temperature of the biological tissue can be correlated with a temperature change of the biological tissue. For example, as explained above, the 1450 nm water absorption peak for cancerous human skin tissue exhibited a blue shift of 4±1 nm as the temperature increased from 25° C., to 36° C., and 7±1 nm as the tissue temperature increased from 25° C., to 60° C. Therefore, the wavelength of this peak can be monitored as heat is applied to the tissue, and the change of the wavelength as the tissue is heated can be used as an indication of a temperature change of the tissue in response to the applied heat. In other words, rather than, or in addition to, monitoring the absolute value of the peak wavelength as an indicator of a temperature of the tissue, the change of the wavelength as the sample is heated can be used as an indicator of the change in the temperature of the tissue from an initial temperature value.

Although techniques for determining a temperature of a biological tissue sample based on reflectance spectra around the wavelengths of 980 nm, 1200 nm, and 1450 nm have been described above, other spectra also can be used. For example, water absorption peaks near 1960 nm and/or 2940 nm also can be used.

In addition, it has been demonstrated that absorption peaks in the reflectance spectra of cancerous human skin tissue in the vicinity of 980 nm and in the vicinity of 1190 nm are blue shifted compared to the absorption peaks in the reflectance spectra of normal human skin tissue. For example, the blue shift of these peaks for cancerous tissue compared to normal tissue at 36° C. is about 3-4 nm. In some implementations, this relative blue shift can be exploited to classify tissue as cancerous or normal. For example, a probe can be scanned over the tissue as reflectance spectra are measured at different locations of the tissue values of the wavelengths at which peak absorption occurs for the peaks near 980 nm and 1190 nm can be determined for the different locations. Then, the relative blue shifts of the values for different locations relative to other locations can of the used to classify different locations in the tissue as healthy or cancerous. Thus, this differential technique of classifying tissue based on a relative blue shift need not rely explicitly on accurately determining the absolute values of the peak wavelengths, but rather can rely on observations of a blue shift of the reflected spectra from cancerous regions, which can relax the requirement for calibration of the system.

Figure 7B:
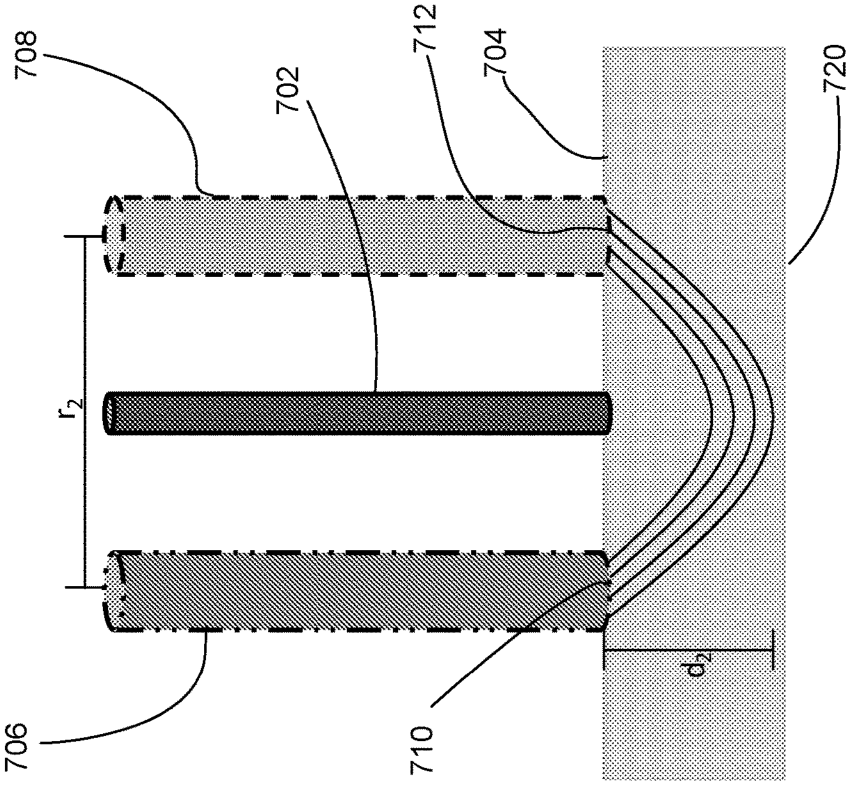
FIG. 7B is a schematic diagram of a second arrangement of the system 700 shown in FIG. 1.
Figure 7A:
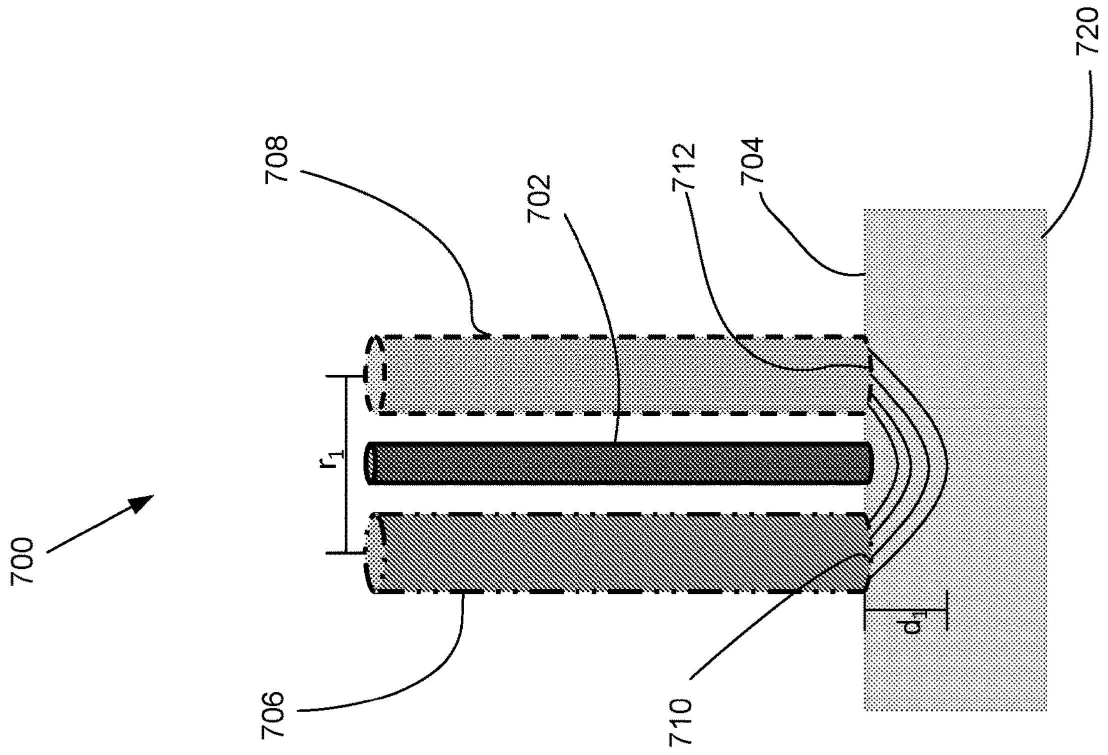
FIG. 7A is a schematic diagram of a first arrangement of a system for providing a thermal therapy to biological tissue and for monitoring a temperature of the tissue while the tissue is heated.

FIG. 7A is a schematic diagram of a first arrangement of a system 700 for providing a thermal therapy to biological tissue and for monitoring a temperature of the tissue while the tissue is heated. The system 700 includes a heating optical fiber 702 that is configured to deliver electromagnetic radiation to a sample 704 to heat the sample 704. The system 700 also includes a light source optical fiber 706 and a signal collection optical fiber 708 that together can be used to monitor a temperature of the sample 704 as heat is delivered to the sample by the heating optical fiber 702. For example, the light source optical fiber 706 can deliver a broad spectrum of light (e.g., 800 nm to 1700 nm) to the sample 704, where the broad spectrum of light is emitted from the fiber 706 and delivered to the sample 704 from a first end 710 of the fiber, were the first end 710 is proximate to the sample 704. The broad spectrum of light from the fiber 706 is reflected from the sample 704, and the reflected light is collected by the signal collection optical fiber 708 through a second end 712 of the fiber 708, where the second end 712 is proximate to the sample 704.

The first end 710 and the second end 712 can be located a distance $r_1$ apart from each other in a direction parallel to a surface of the sample 710. Based on the distance $r_1$, the reflected light that is collected by the signal collection optical fiber 708 is reflected from portions of the sample located at an average depth $d_1$ below the surface of the sample, where the average depth is proportional to the distance $r_1$ between the ends 710, 712.

FIG. 7B is a schematic diagram of a second arrangement of the system 700 shown in FIG. 7A, but where the ends 710, 712 of the fibers 706, 708, respectively, are located at a distance $r_2$ apart from each other in a direction parallel to a surface of the sample 710. Based on the distance $r_2$, the reflected light that is collected by the signal collection optical fiber 708 is reflected from portions of the sample located at an average depth $d_2$ below the surface of the sample. When the distance $r_2$ is greater than $r_1$, then the depth $d_2$, is greater than the depth $d_1$.

Figures 8A, 8B:
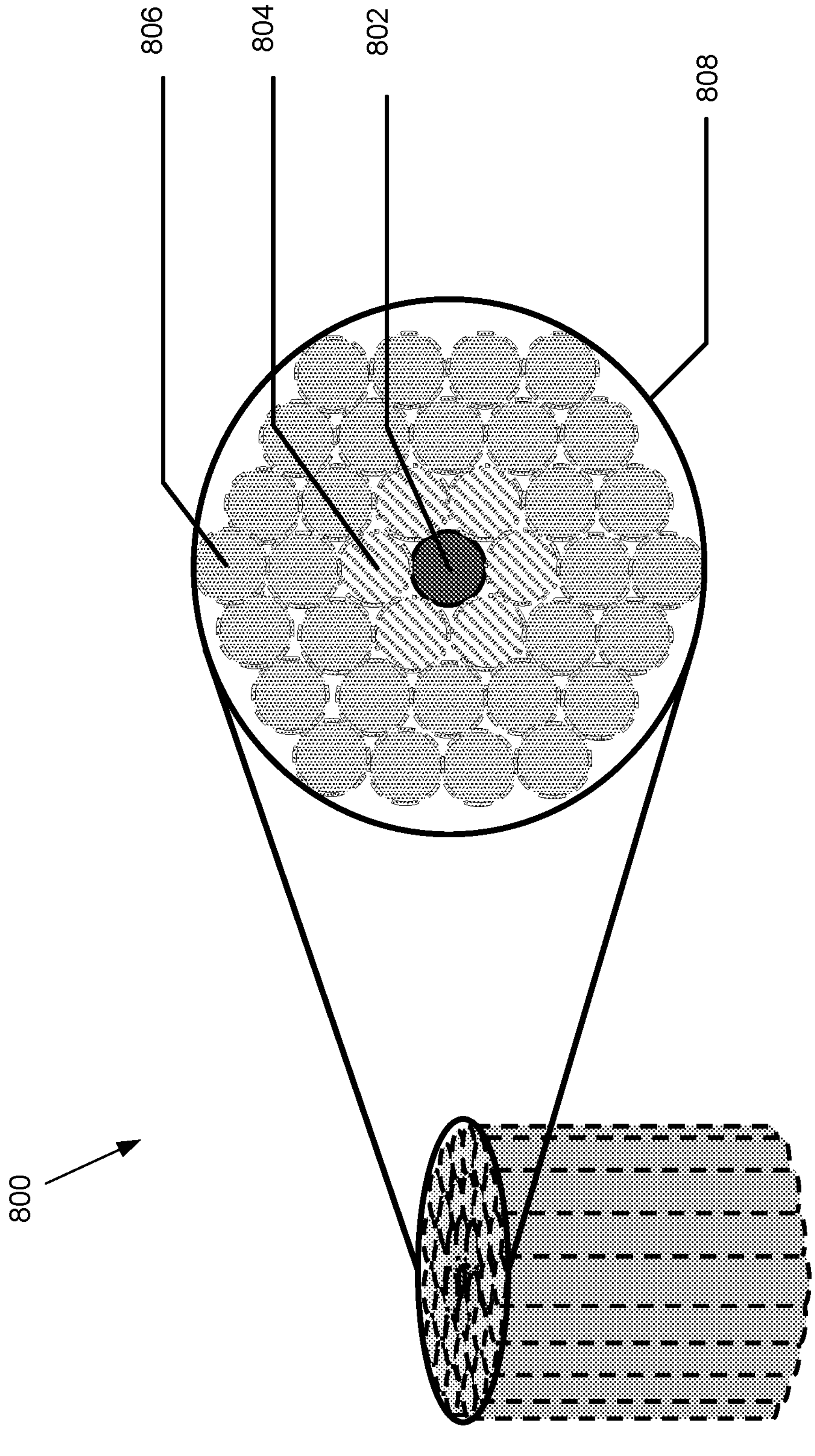
FIG. 8A is a schematic perspective view of a bundle of a plurality of optical fibers.
FIG. 8B is a schematic end view of the bundle of FIG. 8A.

FIG. 8A is a schematic perspective view of a bundle 800 of a plurality of optical fibers, and FIG. 8B is a schematic end view of the bundle 800 of optical fibers of FIG. 8A. The bundle 800 includes a heating optical fiber 802, one or more light source optical fibers 804, and one or more signal collection optical fibers 806. In some implementations, the bundle 800 includes only one light source optical fiber 804 and a plurality of signal collection optical fibers 806. In some implementations, the bundle 800 includes a plurality of light source optical fibers 804 and only one signal collection optical fiber 806. In some implementations, the bundle 800 includes a plurality of light source optical fibers 804 and a plurality of signal collection optical fiber 806. The bundle 800 of optical fibers 802, 804, 806 can be contained within a jacket 808 that encloses a common bundle 808 of the optical fibers.

The heating optical fiber(s) 802 is/are configured to deliver electromagnetic radiation to heat a sample. The light source optical fiber(s) 804 and the signal collection optical fiber(s) 806 can be used together to monitor a temperature of the sample as heat is delivered to the sample by the heating optical fiber 802. For example, broad spectrum of light (e.g., 800 nm to 1700 nm) can be delivered to the sample though a light source optical fiber 804, and the broad spectrum of light from the fiber 804 is reflected from the sample 704, and the reflected light is collected by a signal collection optical fiber 806. The source optical fiber 804 through which the broad spectrum light is delivered and the signal collection optical fiber 806 that collects the reflected light can be selected based on the lateral distance in a direction parallel to a surface of the sample between a first end of the source optical fiber 804 through which the broad spectrum light is delivered and a second end of the signal collection optical fiber 806 that collects the reflected light, where the fibers are selected to determine an average depth within the sample from which the reflected light is collected.

Figure 9:
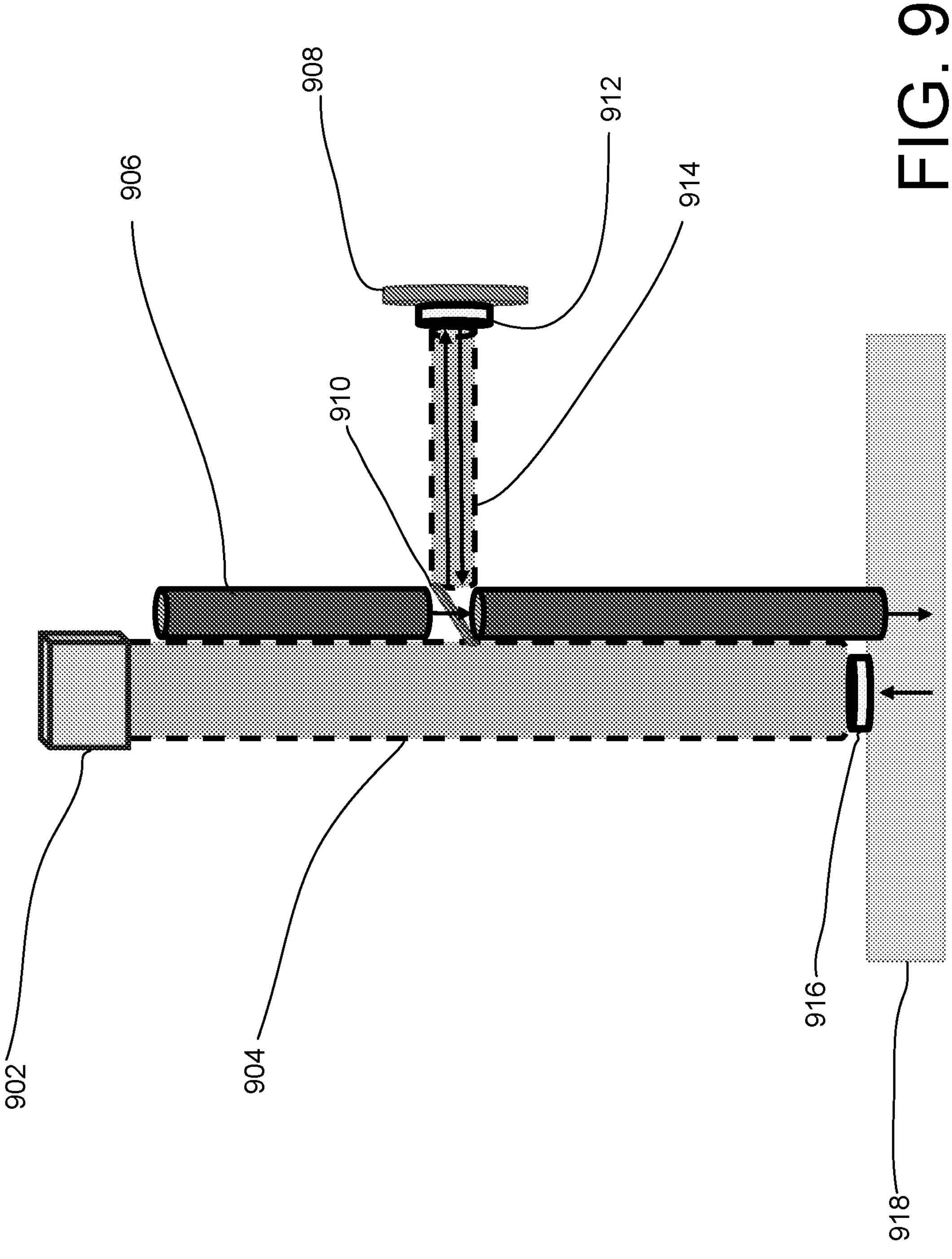
FIG. 9 is a schematic side view of a system for determining a temperature of biological tissue based on reflectance from the biological tissue of therapeutic radiation delivered to the sample.

FIG. 9 is a schematic side view of a system 900 for determining a temperature of a biological tissue sample 918 based on reflectance from the biological tissue of therapeutic radiation delivered to the sample. The system 900 includes one or more treatment optical fibers 906 configured for delivering therapeutic radiation to the sample 918, where the delivered therapeutic radiation raises the temperature of the sample 918. A portion of the therapeutic radiation can be coupled out of the treatment optical fiber(s) 906, for example, by a beam splitter (also known as an output coupler) 910, and delivered, for example by a reference optical fiber 914, to a reference measurement detector 908 that measures an amount of the radiation coupled out of the treatment optical fiber(s) and delivered to the reference measurement detector 908. A portion of the therapeutic radiation is delivered by the treatment optical fiber(s) 906 to the sample 918 to treat the biological sample tissue 918. The amount of radiation measured by the reference measurement detector 908 is proportional to an amount of therapeutic radiation delivered though the optical fiber(s) 906 to the sample 918. In some implementations, prior to being provided to the reference measurement detector 908, the radiation that is coupled out of the treatment optical fiber(s) 906 can be provided to a reflectance standard (e.g., a highly polished, front surface mirror, a 99% spectralon, etc.) and radiation reflected from the reference standard then can be provided to the reference measurement detector 908.

In some implementations, the therapeutic radiation can be provided in pulses, and relatively long pulses, and/or relatively more pulses, can be delivered to the sample 918, while relatively short pulses, and/or relatively fewer pulses, can be delivered to the reference measurement detector 908. The system 900 can include an attenuator 912 placed in front of the reference measurement detector 908 to reduce the intensity of radiation received at reference measurement detector 908 to prevent damage to the reference.

One or more collection optical fibers 904 can collect treatment radiation reflected from the sample 918 and provide the collected reflected radiation to a detector 902. An attenuator 916 can placed in the path between the sample 918 and the detector 902 to prevent damage to the detector 902 and/or to optical elements in the path, including the optical fiber(s) 904. Reference signal measured at the reference measurement detector 908 and radiation reflected from the sample 918 and measured at the detector 902 can be measured approximately simultaneously (e.g., within 100 milliseconds), so that the amount of reflected radiation detected at detector 902 can be calibrated against the amount of radiation measured at the reference measurement detector 908 and used to determine a percentage of treatment radiation reflected from the sample 918 during therapeutic treatment. For example, a controller can determine a proportion, or percentage, of collected radiation in relation to the amount of radiation provided to the sample. As described above, because the percentage of radiation that is reflected from the sample depends on the temperature of the sample, at least when the wavelength of radiation is close to a water absorption peak, the measurement of the percentage of reflected radiation can be used to determine a temperature of the sample. This technique determining a temperature of the sample based on an amount of reflected radiation can be used, even for narrow bandwidth illumination of the sample, as may be the case when treating the sample with radiation from a high power laser.

Figure 10:
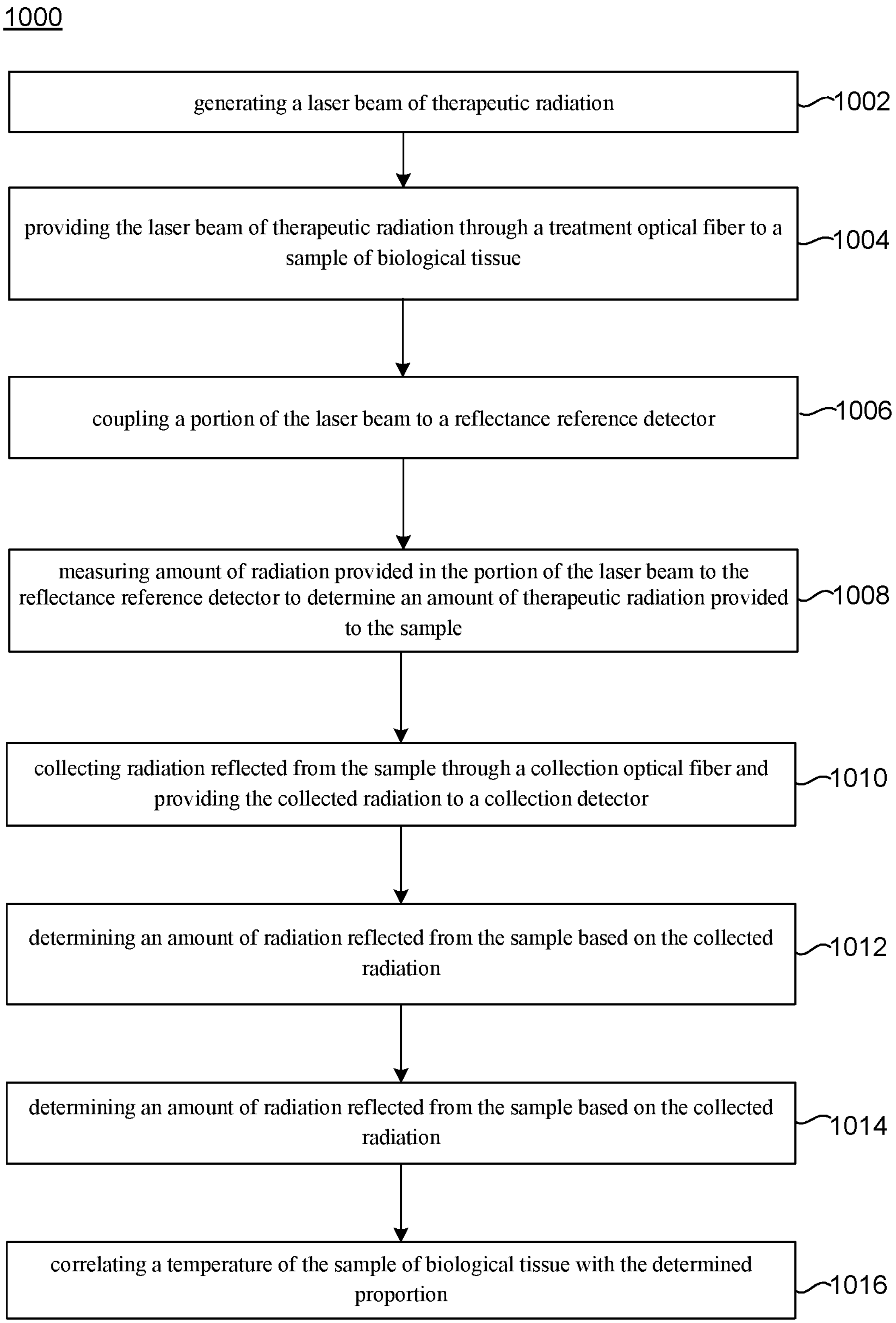
FIG. 10 is a flowchart of a process according to an aspect of the disclosure.

FIG. 10 is a flowchart of a process 1000 according to an aspect of the disclosure. The process 1000 includes generating a laser beam of therapeutic radiation (1002) and providing the laser beam of therapeutic radiation through a treatment optical fiber to a sample of biological tissue (1004). The process 1000 further includes coupling a portion of the laser beam to a reflectance reference detector (1006) and measuring amount of radiation provided in the portion of the laser beam to the reflectance reference detector to determine an amount of therapeutic radiation provided to the sample (1008). The process further includes collecting radiation reflected from the sample through a collection optical fiber and providing the collected radiation to a collection detector (1010) and determining an amount of radiation reflected from the sample based on the collected radiation (1012). The process 1000 also includes determining a proportion of collected radiation in relation to the amount of radiation provided to the sample (1014) and correlating a temperature of the sample of biological tissue with the determined proportion (1016).

Figure 11:
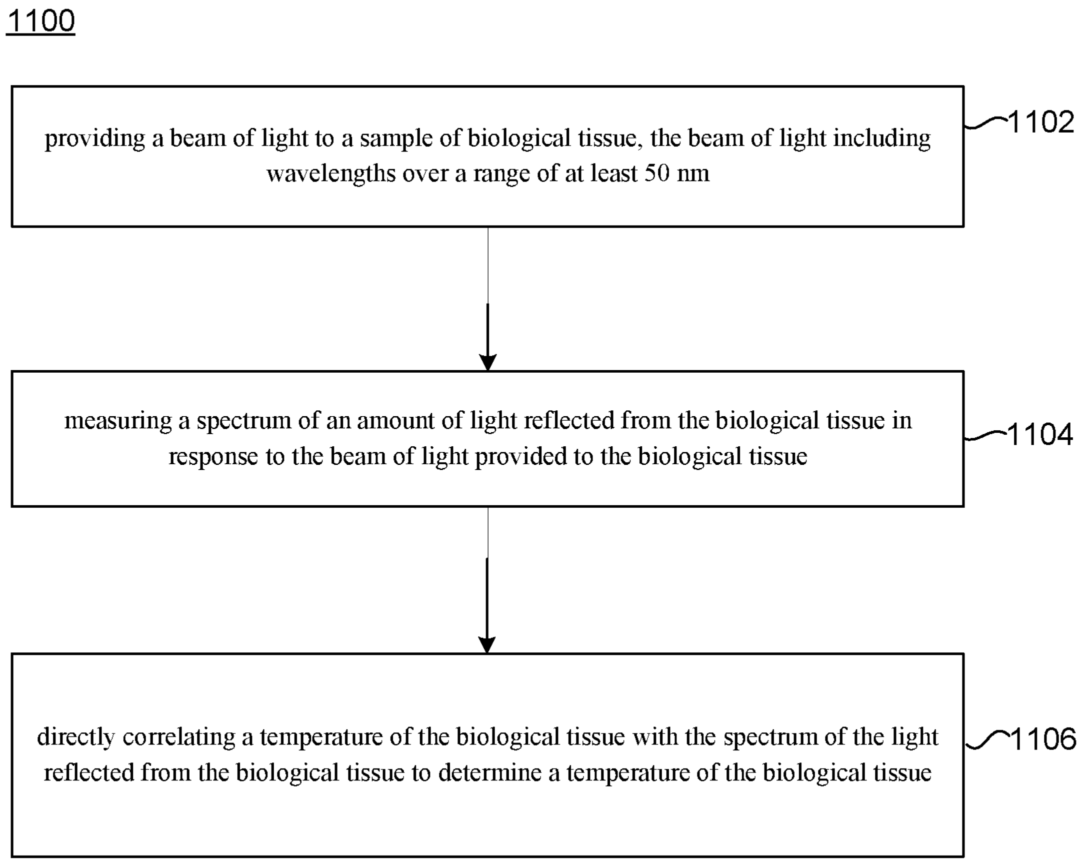
FIG. 11 is a flowchart of a process according to an aspect of the disclosure.

FIG. 11 is a flowchart of a process 1100 according to an aspect of the disclosure. The process 1100 includes providing a beam of light to a sample of biological tissue, the beam of light including wavelengths over a range of at least 50 nm (1102), measuring a spectrum of an amount of light reflected from the biological tissue in response to the beam of light provided to the biological tissue (1104), and directly correlating a temperature of the biological tissue with the spectrum of the light reflected from the biological tissue to determine a temperature of the biological tissue (1106).

While certain features of the described implementations have been illustrated as described herein, many modifications, substitutions, changes and equivalents will now occur to those skilled in the art. It is, therefore, to be understood all such modifications and changes as fall within the true spirit of the various implementations.

What is claimed is:

1. A system comprising:

a light source configured to provide a beam of light to a sample of biological tissue, the beam of light including wavelengths over a range of at least 50 nm;

a spectrometer configured for measuring a spectrum of an amount of light reflected from the biological tissue in response to the beam of light provided to the biological tissue; and a controller configured for directly correlating a temperature of the biological tissue with one or more of: a wavelength or slope in the measured spectrum to determine a temperature of the biological tissue without calculating any of: an absorption coefficient, a scattering coefficient, or an anisotropy factor of the biological tissue from the spectrum.

2. The system of claim 1, wherein correlating the temperature of the biological tissue with one or more of: a wavelength or slope in the spectrum of the light reflected from the biological tissue includes correlating at least a slope of the spectrum with the temperature of the biological tissue.

3. The system of claim 1, further comprising an optical fiber configured for providing the beam of light to the biological tissue.

4. The system of claim 1, further comprising an optical fiber configured for providing the light reflected from the biological tissue to the spectrometer.

5. The system of claim 1, further comprising:

at least one illuminating optical fiber, each illuminating optical fiber being configured for providing the beam of light to the biological tissue, each of the at least one illuminating optical fiber including a first end located proximate to the biological tissue from which the beam of light is provided to the biological tissue; and a plurality of detection optical fibers, each detection optical fiber having a second end configured for collecting the light reflected from the biological tissue and for providing the collected light to the spectrometer.

6. The system of claim 5, wherein each of the second ends is located at a different distance from the first end from which the beam of light is provided to the sample of biological tissue.

7. The system of claim 5, further comprising: a heating optical fiber configured for providing electromagnetic radiation to the sample of biological tissue to heat the sample of biological tissue, wherein each of the illuminating optical fibers, each of the plurality of detection optical fibers, and the heating optical fiber are contained within a common fiber bundle.

8. The system of claim 1, wherein the spectrometer is configured for measuring the spectrum of the amount of light reflected from the biological tissue in response to the beam of light provided to the biological tissue as the biological tissue is heated; and wherein the controller is configured for directly correlating a temperature of the biological tissue with a change of spectrum of the light reflected from the biological tissue as the biological tissue is heated to determine a temperature of the biological tissue.

9. The system of claim 8, wherein the change in the spectrum includes a change in a wavelength of a water absorption peak in the measured spectrum as the biological tissue is heated, and wherein correlating the temperature of the biological tissue with one or more of: a wavelength or slope in the spectrum of the light reflected from the biological tissue includes correlating at least the wavelength of the water absorption peak in the measured spectrum with the temperature of the biological tissue.

10. The system of claim 8, wherein the change in the spectrum includes a change in a slope of the spectrum with the temperature of the biological tissue as the biological tissue is heated, and wherein correlating the temperature of the biological tissue with one or more of: a wavelength or slope in the spectrum of the light reflected from the biological tissue includes correlating at least a slope of the spectrum with the temperature of the biological tissue.

11. A method comprising:

providing a beam of light to a sample of biological tissue, the beam of light including wavelengths over a range of at least 50 nm;

measuring a spectrum of an amount of light reflected from the biological tissue in response to the beam of light provided to the biological tissue; and directly correlating a temperature of the biological tissue with one or more of: a wavelength or slope in the measured spectrum to determine a temperature of the biological tissue without calculating any of: an absorption coefficient, a scattering coefficient, or an anisotropy factor of the biological tissue from the spectrum.

12. The method of claim 11, wherein directly correlating the temperature of the biological tissue with one or more of: a wavelength, shape, or slope in the spectrum of the light reflected from the biological tissue includes correlating at least a slope of the spectrum with the temperature of the biological tissue.

13. The method of claim 11, further comprising:

providing the beam of light to the sample of biological tissue in an illuminating optical fiber; and collecting the reflected light in a collection optical fiber of a plurality of collection optical fibers, each collection optical fiber having a second end configured for collecting the light reflected from the sample of biological tissue and for providing the collected light to a collection detector and wherein each of the second ends is located at a different distance from a first end of a treatment optical fiber from which the beam of light is provided to the sample of biological tissue, and the method further comprising:

selecting the collection optical fiber from the plurality of collection optical fibers, the collection optical fiber being selected to define an average depth of the sample from which the collected light is collected.

14. The method of claim 11, further comprising providing electromagnetic radiation to the sample of biological tissue to heat the sample of biological tissue.

15. The method of claim 14, wherein:

directly correlating the temperature of the biological tissue with the spectrum of the light reflected from the biological tissue to determine a temperature of the biological tissue includes directly correlating a temperature of the biological tissue with a change of spectrum of the light reflected from the biological tissue as the biological tissue is heated to determine a temperature of the biological tissue.

16. The method of claim 15, wherein the change in the spectrum includes a change in a wavelength of a water absorption peak in the measured spectrum as the biological tissue is heated, and wherein correlating the temperature of the biological tissue with one or more of: a wavelength or slope in the spectrum of the light reflected from the biological tissue includes correlating at least the wavelength of the water absorption peak in the measured spectrum with the temperature of the biological tissue.

* * * * *